(12) United States Patent
Kleinwaechter et al.

(10) Patent No.: US 11,166,917 B2
(45) Date of Patent: Nov. 9, 2021

(54) DIRECT INJECTION MOLDABLE AND RAPIDLY DISINTEGRATING TABLET MATRIX

(75) Inventors: Daniela Kleinwaechter, Darmstadt (DE); Guenter Moddelmog, Reinheim (DE); Roberto Ognibene, Darmstadt (IT)

(73) Assignee: Merck Patent GmbH, Darmstadt (DE)

( * ) Notice: Subject to any disclaimer, the term of this patent is extended or adjusted under 35 U.S.C. 154(b) by 160 days.

(21) Appl. No.: 13/000,241

(22) PCT Filed: May 25, 2009

(86) PCT No.: PCT/EP2009/003677
§ 371 (c)(1),
(2), (4) Date: Dec. 20, 2010

(87) PCT Pub. No.: WO2009/152922
PCT Pub. Date: Dec. 23, 2009

(65) Prior Publication Data
US 2011/0091545 A1    Apr. 21, 2011

(30) Foreign Application Priority Data

Jun. 20, 2008  (EP) .................................... 08011238
Aug. 11, 2008  (EP) .................................... 08014287

(51) Int. Cl.
*A61K 9/20*    (2006.01)
*A61K 9/00*    (2006.01)

(52) U.S. Cl.
CPC .......... *A61K 9/2018* (2013.01); *A61K 9/0056* (2013.01); *A61K 9/2054* (2013.01)

(58) Field of Classification Search
CPC .................................................. A61K 9/0056
See application file for complete search history.

(56) References Cited

U.S. PATENT DOCUMENTS

| | | | |
|---|---|---|---|
| 5,958,471 A | 9/1999 | Schwarz et al. | |
| 6,149,941 A | 11/2000 | Schwarz et al. | |
| 6,165,511 A | 12/2000 | Schwarz et al. | |
| 6,316,029 B1 | 11/2001 | Jain et al. | |
| 6,845,571 B1 | 1/2005 | Schwarz et al. | |
| 6,998,482 B2 | 2/2006 | Erdmann et al. | |
| 7,282,217 B1 * | 10/2007 | Grimshaw et al. | 424/479 |
| 7,510,728 B2 * | 3/2009 | Koike | 424/464 |
| 2002/0071864 A1 * | 6/2002 | Kim et al. | 424/464 |
| 2003/0114717 A1 | 6/2003 | Erdmann et al. | |
| 2003/0118642 A1 * | 6/2003 | Norman et al. | 424/465 |
| 2004/0071772 A1 | 4/2004 | Narita et al. | |
| 2004/0162333 A1 | 8/2004 | Mezaache et al. | |
| 2005/0008693 A1 | 1/2005 | Erdmann et al. | |
| 2006/0165781 A1 | 7/2006 | Ferran | |
| 2009/0022794 A1 | 1/2009 | Johannes | |
| 2009/0028943 A1 * | 1/2009 | Cahill et al. | 424/474 |
| 2009/0186081 A1 | 7/2009 | Holm et al. | |
| 2010/0167052 A1 * | 7/2010 | Satomi et al. | 428/402 |

FOREIGN PATENT DOCUMENTS

| | | | |
|---|---|---|---|
| CN | 1494419 | 5/2004 | |
| DE | 44 39 858 | 5/1996 | |
| DE | 44 39 858 A1 | 5/1996 | |
| EP | 0 738 252 B1 | 10/1995 | |
| EP | 0 738 252 | 10/1996 | |
| EP | 0 904 059 B1 | 4/1997 | |
| EP | 0 869 528 B1 | 10/1997 | |
| EP | 0 896 528 | 2/1999 | |
| EP | 0 904 059 | 3/1999 | |
| EP | 1 319 644 B1 | 8/2002 | |
| EP | 1 319 644 | 7/2003 | |
| EP | 1 453 781 B1 | 10/2003 | |
| EP | 1 453 781 | 9/2004 | |
| JP | 2001-163770 | * 8/1999 | |
| JP | 2001163770 A | 6/2001 | |
| JP | 2003533465 A | 11/2003 | |
| JP | 2005306770 A | 11/2005 | |
| JP | 2005325040 A | 11/2005 | |
| JP | 2005533045 A | 11/2005 | |
| WO | WO-96 14282 | 5/1996 | |
| WO | WO-97 39739 | 10/1997 | |
| WO | WO-97 41835 | 11/1997 | |
| WO | WO 00/76650 A1 | 6/2000 | |
| WO | WO-00 76650 | 12/2000 | |
| WO | WO-03/055834 | 7/2003 | |
| WO | WO-2006 097946 | 9/2006 | |
| WO | WO2006/097946 A | 9/2006 | |
| WO | WO-2006103407 A2 * | 10/2006 | ............ A61K 9/006 |
| WO | 2007029376 A1 | 3/2007 | |
| WO | 2007060402 A1 | 5/2007 | |
| WO | WO2007/060402 | * 5/2007 | |

(Continued)

OTHER PUBLICATIONS

EMPROVE Parteck M 200, accessed Jul. 9, 2012.*
Machine Translation of JP2001-163770, espacenet, accessed Nov. 14, 2014.*
Technical Information 100419: Parteck® M 200. Merck KGaA, Germany (Feb. 2013).*
Technical Information 100490: Parteck® ODT. Merck KGaA, Germany (Jul. 2012).*
Remington: The Science and Practice of Pharmacy. 21st Edition (2005) pp. 891-893 and 929-932.*
International Search Report of PCT/EP2009/003677, Date of Completion Oct. 13, 2009, dated Oct. 20, 2009.

(Continued)

*Primary Examiner* — Bethany P Barham
*Assistant Examiner* — Peter Anthopolos
(74) *Attorney, Agent, or Firm* — Millen, White, Zelano & Branigan, PC; Ryan Pool

(57) ABSTRACT

The present invention relates to a novel directly compressible matrix for the production of tablets which disintegrate rapidly in the presence of moisture, in particular in the mouth.

19 Claims, 1 Drawing Sheet

(56) References Cited

FOREIGN PATENT DOCUMENTS

| WO | WO-2007 076874 | 7/2007 |
|---|---|---|
| WO | WO2007/076874 A | 7/2007 |

OTHER PUBLICATIONS

Journal of American Chemical Society, by. Stephen Brunauer, P.N. et al., Adsorption of Gases in Multimolecular Layers. pp. 309-319.

Brunauer, S. et al., "Adsorption of gases in multimolecular layers," Journal of the American Chemical Society, 1938, vol. 60, No. 9, pp. 309-319.

Examination Report related to corresponding Chilean Patent Application No. 2009-001450, dated May 30, 2014.

Official Action related to corresponding Japanese Patent Application No. 2011-513898, dated Feb. 25, 2014.

Shu et al, 'Studies of Rapidly disintegrating tablets in the oral cavity using co-ground mixtures of mannitol with Crospovidone'; Chem. Pharm. Bull., 50(2), 193-198, 2002.

Handbook of Pharmaceutical excipients, 5th Edition, ED. Rowe, Sheskey and Owen; ISBN 1582120587; pub. 2006, pp. 211-213 and 449-453.

Jacob et al., "Novel co-processed excipients of mannitol and microcrystalline cellulose for preparing fast dissolving tablets of glipizide" Indian J Pharm Sci, 2007, 69, 5, pp. 633-639.

Jin et al., "pharmaceutical evaluation of fast-disintegrant tablet . . . " Abstract Acta Pharmaceutica Sinica, 2001, 36, 7, 535-538

Office Action in corresponding Brazil application P10914164-2 dated Sep. 1, 2018 (pp. 1-9).

\* cited by examiner

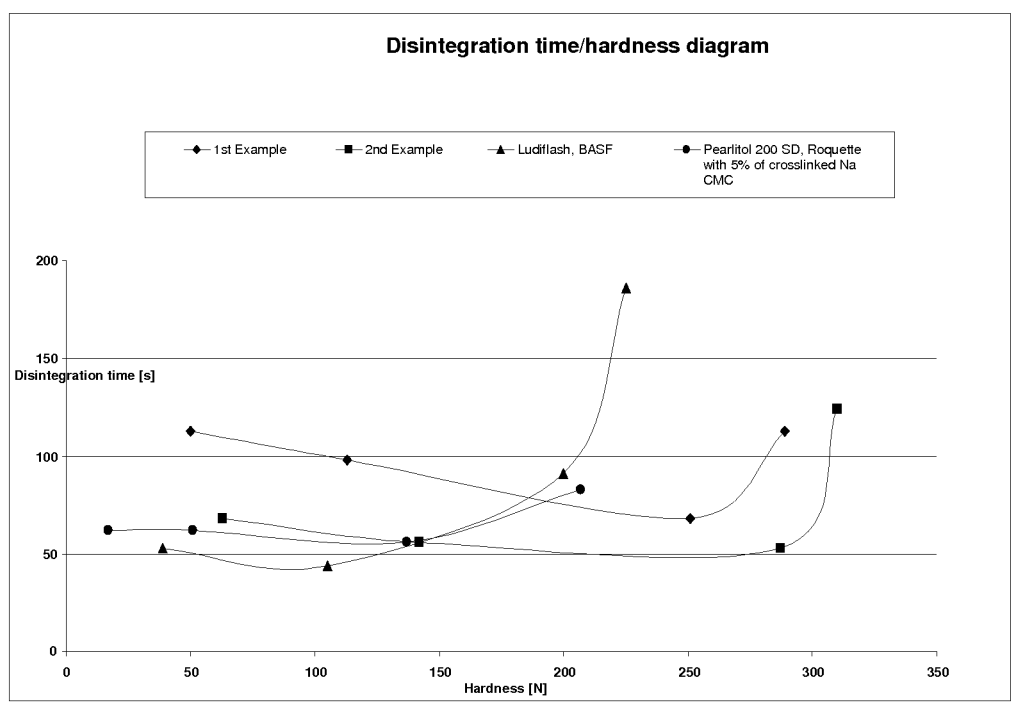

DIRECT INJECTION MOLDABLE AND RAPIDLY DISINTEGRATING TABLET MATRIX

The present invention relates to a novel directly compressible matrix for the production of tablets which disintegrate rapidly in the presence of moisture.

PRIOR ART

For the rapid release of active compound from solid oral medicament formulations, in particular from tablets, a tablet matrix which disintegrates very rapidly, has a pleasant taste and is simple to process is needed. At the same time, this matrix must provide, through compression, sufficiently hard tablets having low abrasion in order to make them easy to handle for further processing after their production, such as, for example, for packing and for the patient.

Mannitol is an obvious choice as the basis for such a matrix since, after suitable pretreatment, it readily compressible, has good storage stability, is compatible with virtually all active compounds and at the same time has a pleasant sweet taste.

However, the mannitol preparations currently available on the market for this application either have a very complex structure and/or are inadequate in their pharmaceutical formulation properties.

OBJECTIVE

Two contradictory requirements of such a tablet matrix, namely high tablet hardnesses at the same time as very rapid disintegration and release of the active compounds, have to be combined in a suitable preparation of this type. Furthermore, the matrix should be very simple to process in industrial tablet manufacture, so that it can be compressed directly with the other tablet components without granulation steps.

Achievement of the Object

Experiments have now shown that the provision of a co-mixture of a specific mannitol powder with crosslinked sodium carboxymethylcellulose gives a tablet matrix having a specific grain structure and a large BET surface area for the production of rapidly disintegrating tablets in a direct tableting process.

The present invention thus relates to a co-mixture for the production of rapidly disintegrating tablets in a direct tableting process, consisting of 90 to 98 parts by weight, particularly preferably 95 parts by weight, of a sprayed mannitol and 10 to 2 parts by weight, particularly preferably 5 parts by weight, of a crosslinked sodium carboxymethylcellulose, which is characterised in that it has a BET surface area of greater than 1.5 $m^2/g$. It has proven particularly advantageous to use mixtures whose BET surface area is in the range from 1.9 to 4.0 $m^2/g$, in particular in the range from 1.9 to 2.6 $m^2/g$. It has proven very particularly advantageous to employ corresponding mixtures for the production of tablets which simultaneously have a bulk density in the range from 0.45 to 0.60 g/ml, a tapped density in the range from 0.60 to 0.75 g/ml, and an angle of repose in the range from 30 to 38°.

In such co-mixtures according to the invention, the particles can have average particle diameters (laser determination) in the range between 60 and 200 µm, preferably in the range 64-114 µm. The mixture to be employed preferably has a water content <1% by weight.

Co-mixtures which have these properties can be compressed to give tablets in a simple manner. After compression at a pressing force of 20 kN, it is possible to obtain tablets having hardnesses of >250N which have a friability≤0.14% and a disintegration time≤70 seconds.

In particular, the co-mixtures according to the invention are suitable for use as excipient material for active compound- and/or aroma-containing tablet formulations which have the said advantageous properties, and tablets or other pharmaceutical formulations with or without active compound prepared from this excipient material.

Owing to their advantageous properties, the excipient materials according to the invention are particularly suitable for use for the preparation of tablet formulations which comprise active compounds and aromas. These may be, in particular:

- substances from the area of food supplements, such as, for example, vitamins, mineral substances, trace elements, functional food constituents, for example plant constituents and plant extracts
- substances from the area of synthetic and natural dyes, natural and nature-identical aromas and other flavouring substances, such as, for example, sweeteners (aspartame, sachcharine, acesulfame K, neohesperidin DC, sucralose; thaumatin, stevioside), fruit aromas, peppermint aromas or menthol, fruit acids, such as citric acid and tartaric acid, flavouring plant extracts, etc.
- substances having a pharmacological action, such as, for example, antacids, antiinfectives, which are also employed for local action in the mouth and throat area, analgesics, including opioids, antiallergics, antiemetics, antidiarrhoeal agents, etc.

DETAILED DESCRIPTION OF THE INVENTION

By combination (mixing) of a sprayed mannitol (Parteck M, Merck KGaA) with a so-called superdisintegrant, for example crosslinked Na CMC (Ac-Di-Sol, FMC BioPolymer), a directly compressible tablet matrix can be obtained which exhibits constantly low disintegration properties over a very broad hardness range. These very short disintegration times can be maintained over a significantly broader hardness range than is the case with co-sprayed mannitol/disintegrant combinations (for example Ludiflash; BASF) or by blending with other commercially available directly compressible mannitol grades (DC mannitol) with crosslinked Na CMC. It is also surprising that the direct compression properties (DC properties) of the mannitol do not suffer due to the mixing operation, in spite of the considerable mechanical load.

With the material obtained, the further processor can therefore obtain very rapidly disintegrating tablets, for example ODT (orally dispersible tablet), in a simple manner by simple blending with his recipe constituents and subsequent direct compression. This very rapid disintegration is an essential prerequisite for rapid release of active compound together with rapid absorption of the API, for example already in the mouth and throat area.

Blending (for example in a screw-and-cone mixer) of a combination consisting of 90-98 parts by weight of Parteck M (preferably Parteck M200) with 10-2 parts by weight of a superdisintegrant, preferably with crosslinked Na CMC, for example Ac-Di-Sol, meets these requirements in an excellent manner. The best results with respect to the hardness/disintegration time ratio are obtained with a combination consisting of 95% of Parteck M200 and 5% of Ac-Di-Sol type SD-711; FMC BioPolymer.

The pulverulent mannitol which can be employed in accordance with the invention can be prepared by a process known from the patent specification EP 0 896 528 B1. The preparation is preferably carried out by a corresponding spray-drying process. However, it can also be carried out by fluidised-bed granulation. The process is carried out per se by a) preparing an aqueous mannitol solution, which may optionally comprise a further polyol in a small amount, optionally in an amount of up to 2% by weight, based on the total amount of mannitol and further polyol, and b1) spraying the resultant solution in an air stream having a temperature between 120 and 300° C., during which the water of the solution is evaporated, or b2) fluidising the resultant solution in an air stream having a temperature between 40 and 150° C., during which the water of the solution is evaporated.

The spraying is carried out by atomisation by means of nozzles, preferably by means of a centrifugal atomiser, into a dry air stream blown in centrifugally and warmed to a temperature of 120 to 300° C., preferably 140 to 190° C. The amount of polyol solution supplied and of hot air blown in is matched to one another in such a way that the polyol is dried to a water content of about 0.3 to about 1% by weight. In any case, the water content should be below 1% by weight.

The polyol agglomerates obtained by removal of water from the polyol solution droplets are warmed to a temperature of about 50 to about 70° C. during the spray drying, while the air blown in cools to approximately the same temperature. The mannitol grade prepared in this way is collected in containers and, after cooling, is directly suitable for the production of tablets or lozenges.

However, it is also possible to carry out the preparation of the mannitol which can be employed in accordance with the invention in a continuous procedure in a plant having a fluidised bed for post-drying of the spray-dried material, optionally with powder recycling. Corresponding plants are known to the person skilled in the art, such as, for example, from the patent specifications EP 1 453 781 B1 and EP 1 319 644 B1 or from WO 00/76650 A1. Such plants allow the person skilled in the art to set the desired particle size of the granules by specific adjustment of the powder bed, the gas stream, the temperature programme and optionally additional spraying-on of additional starting solution, and controlled product recycling of fine material. Simpler plants are found in the patent specifications EP 0738 252 B1 or EP 0904059 B1.

Besides a filamentous microstructure, the mannitol obtained in this way has a very large surface area. The desired particle-size spectrum of the particles present in the powder prepared can be set specifically through the choice of the operating parameters of the spray-drying plant or fluidised-bed granulation plant. However, it is also possible to separate off oversized and undersized particles by sieving and thus to set the average particle diameters of the mannitol powder in the range from 60 to 200 µm, preferably in the range from 64 to 114 µm. Corresponding methods for sieving under mild conditions are known to the person skilled in the art. Corresponding products are commercially available under the trade name Parteck M, for example Parteck M 200.

As already stated above, experiments have shown that a co-mixture consisting of a mannitol of the grade described and a so-called superdisintegrant in a certain mixing ratio, based on the weight, an excipient material for the production of tablets can be prepared, that, even on compression with a relatively low pressing force, gives tablets having comparatively high tablet hardnesses, but which disintegrate in a relatively short time in the presence of moisture.

A suitable superdisintegrant in this connection has proven to be commercially available crosslinked Na CMC, which is commercially available under various trade names and likewise has small average particle diameters at the same time as a sufficiently large surface area. Crosslinked Na CMC having an average particle diameter in the range from 10 to 100 µm, preferably in the range from 20 to 50 µm, is preferably employed.

Comparative experiments have shown that the products according to the invention, consisting of a mixture of 90-98 parts of Parteck M with 10 to 2 parts of a superdisintegrant, preferably with crosslinked Na CMC, for example Ac-Di-Sol, exhibit improved tablet hardnesses compared with the known sprayed mannitol grades without addition of crosslinked Na CMC as excipient material, in particular in the region of relatively high pressing forces, i.e. that they have, in particular, no tendency towards "capping". In addition, the disintegration times of the products according to the invention are significantly shorter than the tablets obtained using sprayed mannitol grades without addition of Na CMC as excipient material.

Although a co-sprayed product comprising 95 parts of mannitol and 5 parts of crosslinked Na CMC has, compared with the products according to the invention, similar tablet hardnesses (and also exhibits no "capping tendency"), it has, however, significantly longer disintegration times. This comparative material is prepared by the process described by, in a different manner, distributing the crosslinked Na CMC in the mannitol solution to be sprayed in accordance with the mannitol to crosslinked Na CMC ratio 95:5 (as dry substances) and co-spraying it with constant agitation under the conditions described by spray drying or fluidised-bed granulation.

It has also been found that the disintegration times of tablets comprising co-mixtures according to the invention compared with tablets obtained from commercially available products are short over a broader hardness range. The material according to the invention is therefore particularly suitable for the formulation of pharmaceutical compositions in direct tableting processes, in particular also for the production of tablets which rapidly release active compound in the oral cavity.

Furthermore, the use of the co-mixture according to the invention allows tablets which disintegrate relatively rapidly over a larger tablet hardness range to be obtained compared with tablets produced using the co-sprayed mannitol/crospovidone/polyvinyl acetate/povidone (Ludiflash) obtained commercially for ODT formulations. In addition, as already mentioned, higher tablet hardnesses can be achieved with the mixtures according to the invention on application of comparable pressing forces. This is particularly advantageous to the formulation pharmacist for the formulation of poorly compressible active compounds and enables him to carry out the tableting more easily.

However, Pearlitol 200 SD, which is likewise a sprayed mannitol, also exhibits poorer tableting behaviour after blending with AcDiSol compared with the co-mixture according to the invention, as do other directly compressible mannitol grades on a crystalline or granulated basis, which are distinguished by even poorer binding properties, in particular high friabilities.

The results of the tableting experiments according to the invention carried out and the comparative examples are shown in graph form in FIG. 1, where the disintegration time of the tablets produced are plotted against the tablet hardnesses obtained.

On use of the co-mixtures according to the invention as matrix for tablet production, harder tablets can advantageously be obtained at comparable pressing forces compared with the use of excipient materials which are known to the person skilled in the art from the literature and the trade.

It has furthermore been found that very good binding properties are already obtained through the use of the material according to the invention if tableting is carried out in a preferred low pressing-force range of up to 20 kN in order to protect the tableting dies and tableting machines as far as possible. In addition, the tablets obtained exhibit very good mechanical stability, measured as friability with significantly <1%, meaning that safe handling of the compacts is ensured.

The present description enables the person skilled in the art to apply the invention extensively. Even without further comments, it is therefore assumed that a person skilled in the art will be able to utilise the above description in the broadest scope.

In the case of any lack of clarity, it goes without saying that the publications and patent literature cited should be referred to. Accordingly, these documents are regarded as part of the disclosure content of the present description.

For better understanding and in order to illustrate the invention, two examples are given below which are within the scope of protection of the present invention. These examples also serve to illustrate possible variants. Owing to the general validity of the inventive principle described, however, the examples are not suitable for reducing the scope of protection of the present application to these alone.

It furthermore goes without saying to the person skilled in the art that, both in the examples given and also in the remainder of the description, the component amounts present in the compositions always only add up to 100% by weight or mol %, based on the composition as a whole, and cannot exceed this, even if higher values could arise from the percentage ranges indicated. Unless indicated otherwise, % data are therefore regarded as % by weight or mol %, with the exception of ratios, which are shown in volume data.

The temperatures given in the examples and description and in the Claims are always in ° C.

EXAMPLES

The following analytical methods are used for characterisation of the material:

Bulk density: in accordance with DIN EN ISO 60
Tapped density: in accordance with DIN EN ISO 787-11: 1995
Angle of repose: in accordance with DIN ISO 4324
Determination of the particle size distribution: laser scattering with dry dispersal using a Mastersizer 2000 version 5.10 G, Serial Number: 34403-97 from Malvern Instruments Ltd; Scirocco 2000 (A) dispersion unit, counterpressure 1 bar; evaluation model: Universal; Fraunhofer; performance as described in the technical manual and specifications from the manufacturer
Tableting test:
5 g of Parteck LUB MST (vegetable magnesium stearate) EMPROVE exp PhEur, BP, JP, NF, FCC Art. No. 1.00663 (MERCK KGaA, Germany) are added to 495 g of the material to be tested for its tableting properties, the magnesium stearate is deposited in advance via a 250 µm sieve, and mixed for 5 minutes in a sealed stainless-steel container [capacity: about 2 l, height: about 19.5 cm, diameter: about 12 cm, external sizes] in a laboratory tumble mixer [Turbula, Willy A. Bachofen (Switzerland)]. The compression to give 500 mg tablets (11 mm punch, round, flat, with bevel) is carried out on a Korsch EK 0-DMS (KORSCH, Germany) instrumented eccentric tableting machine with the Catman 5.0 evaluation system from Hottinger Baldwin Messtechnik—HBM (Germany).

Depending on the pressing force used (5, 10, 20 and 30 kN; in each case +/−10%), at least 100 tablets are produced for evaluation of the pharmaceutical formulation characteristic numbers.

Determination of the tablet hardnesses, diameters and heights: Erweka TBH 30 MD; Erweka (Germany); average data from in each case 20 tablet measurements per pressing force Tablet abrasion: Erweka (Germany) friability tester; instrument parameters and performance of the measurements in accordance with Ph Eur 5th Edition "Friability of uncoated tablets"

Tablet weight: average value from the weighing of 20 tablets; balance: Mettler AT 201 Mettler (Germany)

Tablet disintegration: disi 4 automated tablet tester from Biomation (Germany); medium: deionised water at 37° C.; instrument parameters and performance in accordance with Ph Eur 5th Edition "Disintegration time of tablets and capsules"

BET surface area: evaluation and performance in accordance with the literature "BET Surface Area by Nitrogen Absorption", S. Brunauer et al. (Journal of American Chemical Society, 60, 9, 1938) and DIN ISO 9277; instruments: ASAP 2420 Micromeritics Instrument Corporation (USA); volumetric method; nitrogen; sample weight about 3 g +/−5% with sample preparation (heating at 3.0° C./min. to the target temperature of 50° C.): 10 hours/50° C.

The handling, storage, further processing and testing of the granules and compacts is carried out at temperatures of 19 to 25° C. and relative humidities in the range from 20 to 35%.

Characterisation: co-mixture of 95 parts by weight of granulated mannitol with 5 parts by weight of crosslinked Na CMC (95:5) (AcDiSol type SD-711; FMC BioPolymer) (2 examples)

|  | Product according to the invention (1st example) | Product according to the invention (2nd example) |
| --- | --- | --- |
| Bulk density | 0.59 g/ml | 0.53 g/ml |
| Angle of repose | 37.8° | 33.1° |
| Tapped density | 0.75 g/ml | 0.66 g/ml |
| Water content | 0.11% by weight | 0.13% by weight |
| BET surface area | 1.9 m²/g | 2.6 m²/g |
| Particle distribution (laser diffraction, % by vol.) | D(0.10): 16 µm<br>D(0.30): 40 µm<br>D(0.50): 64 µm<br>D(0.75): 112 µm<br>D(0.90): 315 µm | D(0.10): 23 µm<br>D(0.30): 72 µm<br>D(0.50): 114 µm<br>D(0.75): 184 µm<br>D(0.90): 269 µm |

Tableting data: co-mixture of granulated mannitol with crosslinked Na CMC 95:5 (2 examples) compared with granulated mannitol without addition of crosslinked Na CMC and compared with co-sprayed mannitol/crosslinked Na CMC 95:5 (ratio in each case in parts by weight)

| Product | Pressing force [kN] | Tablet hardness [N] | Friability [% by weight] | Disintegration [sec] |
|---|---|---|---|---|
| Product according to the invention 1st example | 5 | 50 | 0.70 | 113 |
|  | 10 | 113 | 0.21 | 98 |
|  | 20 | 251 | 0.13 | 68 |
|  | 30 | 289 | 0.12 | 113 |
| Product according to the invention 2nd example | 5 | 63 | 0.22 | 68 |
|  | 10 | 142 | 0.16 | 56 |
|  | 20 | 287 | 0.12 | 53 |
|  | 30 | 310 | 0.13 | 124 |
| 1st example without crosslinked Na CMC | 5 | 69 | 0.51 | 102 |
|  | 10 | 149 | 0.22 | 315 |
|  | 20 | 212 | 0.16 | 257 |
|  | 30 | 160 | 100 (capping) | 203 |
| 2nd example without crosslinked Na CMC | 5 | 91 | 0.19 | 90 |
|  | 10 | 169 | 0.17 | 324 |
|  | 20 | 200 | 0.20 | 210 |
|  | 30 | 179 | 74.81 (capping) | 266 |
| Co-sprayed mannitol with crosslinked Na CMC (AcDiSol type SD-711) 95:5 | 5 | 53 | 0.67 | 48 |
|  | 10 | 107 | 0.12 | 199 |
|  | 20 | 234 | 0.05 | 434 |
|  | 30 | 343 | 0.08 | 479 |

The products according to the invention exhibit improved tablet hardness, in particular in the region of relatively high pressing forces, compared with the sprayed mannitol grades without addition of crosslinked Na CMC, i.e. in particular no "capping tendency". In addition, the disintegration times of the products according to the invention are significantly faster.

Although a co-sprayed product comprising 95 parts by weight of mannitol and 5 parts by weight of crosslinked Na CMC gives, compared with the products according to the invention, similar tablet hardnesses (and also exhibits no "capping tendency"), the disintegration times are, however, significantly increased.

Tableting data: products according to the invention (2 examples) compared with co-mixtures comprising directly compressible mannitol grades on the market (Pearlitol 200 SD, Pearlitol 300, Mannogem 2080, Mannogem 3215) with Na CMC (AcDiSol type SD-711) 95:5 (parts by weight) and compared with a directly tabletable co-spraying consisting of mannitol/|crospovidone/|polyvinyl acetate/povidone (Ludiflash) praised for ODT formulations

| Product | Pressing force [kN] | Tablet hardness [N] | Friability [% by weight] | Disintegration [sec] |
|---|---|---|---|---|
| Product according to the invention 1st example | 5 | 50 | 0.70 | 113 |
|  | 10 | 113 | 0.21 | 98 |
|  | 20 | 251 | 0.13 | 68 |
|  | 30 | 289 | 0.12 | 113 |
| Product according to the invention 2nd example | 5 | 63 | 0.22 | 68 |
|  | 10 | 142 | 0.16 | 56 |
|  | 20 | 287 | 0.12 | 53 |
|  | 30 | 310 | 0.13 | 124 |
| Co-spraying of mannitol/crospovidone/ polyvinyl acetate/povidone (Ludiflash, BASF) | 5 | 39 | 1.26 | 53 |
|  | 10 | 105 | 0.25 | 44 |
|  | 20 | 200 | 0.15 | 91 |
|  | 30 | 225 | 0.14 | 186 |
| Co-mixture of DC mannitol (Pearlitol 200 SD) with crosslinked Na CMC 95:5 | 5 | 17 | 4.48 | 62 |
|  | 10 | 51 | 0.32 | 62 |
|  | 20 | 137 | 0.15 | 56 |
|  | 30 | 207 | 0.10 | 83 |
| Co-mixture of DC mannitol (Pearlitol 300 DC; Roquette) with crosslinked Na CMC 95:5 | 5 | 24 | 3.93 | 149 |
|  | 10 | 56 | 0.38 | 138 |
|  | 20 | 121 | 0.21 | 115 |
|  | 30 | 103 | 75.30 (capping) | 143 |
| Co-mixture of DC mannitol (Mannogem 2080; SPI) with crosslinked Na CMC 95:5 | 5 | 13 | 42.00 | 104 |
|  | 10 | 35 | 2.14 | 96 |
|  | 20 | 70 | 45.88 (capping) | 75 |
|  | 30 | 69 | 80.54 (capping) | 84 |
| Co-mixture of DC mannitol (Mannogem 3215; SPI) with crosslinked Na CMC 95:5 | 5 | 12 | 95.44 | 69 |
|  | 10 | 38 | 1.67 | 66 |
|  | 20 | 79 | 0.42 | 61 |
|  | 30 | 75 | 85.34 (capping) | 71 |

Compared with the co-sprayed mannitol/crospovidone/polyvinyl acetate/povidone (Ludiflash) praised for ODT formulations, tablets which disintegrate relatively rapidly over a higher tablet hardness range can be obtained with the product according to the invention. In addition, higher tablet hardnesses can be achieved with the product according to the invention at comparable pressing forces, which means a simplification for the formulation pharmacist in the formulation of poorly compressible active compounds.

Pearlitol 200 SD, likewise a sprayed mannitol, likewise exhibits poorer tableting behaviour compared with the product according to the invention, as do the other directly compressible mannitol grades on a crystalline or granulated basis, which are distinguished by even poorer binding properties (in particular high friabilities).

The results of the previous examples and the comparative examples are shown in graph form in FIG. 1, where the disintegration time of the tablets produced are plotted against the tablet hardnesses obtained, i.e. FIG. 1 shows the dependence of the tablet disintegration times on the achievable tablet hardnesses at the 4 pressing forces (5, 10, 20 and 30 kN) of the products according to the invention (2 examples) compared with Ludiflash, BASF and a mixture of Pearlitol 200 SD; Roquette with crosslinked Na CMC (AcDi-Sol type SD-711, FMC BioPolymers) 95:5. The products according to the invention always still exhibit fast disintegration times even at significantly higher tablet hardnesses, in contrast to the two comparisons.

In summary, a harder tablets compared with the prior art at comparable pressing forces can be obtained with the product according to the invention.

The material thus already exhibits very good binding properties in a pressing-force range which is preferred for the greatest possible protection of the tableting dies and tableting machines. The very good mechanical stability—measured as friability with significantly <1%—ensures safe handling of the pressed cores.

At the same time, the disintegration times are low over a broad hardness range compared with tablets obtained from commercially available products on the market. The material according to the invention is therefore particularly suitable for the formulation of pharmaceutical compositions in direct tableting processes, in particular also for the production of tablets which rapidly release active compound in the oral cavity.

BET surface areas: the surface areas, determined by the BET method, of the compared compositions are shown below. As already stated above, these values were determined as described in "BET Surface Area by Nitrogen Absorption", S. Brunauer et al. (Journal of American Chemical Society, 60, 9, 1938) or DIN ISO 9277. The measurements were carried out using instruments from Micromeritics Instrument Corporation (USA) [ASAP 2420]. The measurements were carried out by the corresponding volumetric method using nitrogen (sample weight about 3 g+/−5% with sample preparation (drying by heating to the target temperature of 50° C. at 3.0° C./min.): 10 hours/50° C.).

| | |
|---|---|
| Product according to the invention, 1st example | 1.9 m$^2$/g |
| Product according to the invention, 2nd example | 2.6 m$^2$/g |
| Co-sprayed mannitol with crosslinked Na CMC (AcDuSol type SD-711) 95:5 | 0.5 m$^2$/g |
| Co-spraying mannitol/crospovidone/polyvinyl acetate/povidone (Ludiflash, BASF) | 0.3 m$^2$/g |
| Co-mixture of DC mannitol (Perlitol 200SD; Roquette) with crosslinked Na CMC 95:5 | 0.3 m$^2$/g |
| Co-mixture of DC mannitol (Perlitol 300DC; Roquette) with crosslinked Na CMC 95:5 | 0.6 m$^2$/g |
| Co-mixture of DC mannitol (Mannogem 2080, SPI) with crosslinked Na CMC 95:5 | 0.5 m$^2$/g |
| Co-mixture of DC mannitol (Mannogem 3215, SPI) with crosslinked Na CMC 95:5 | 0.4 m$^2$/g |

The BET data show that the products according to the invention are distinguished by a significantly greater BET surface area compared with other combinations of directly compressible mannitol grades with disintegrant. This increased surface area is combined with very good compressibility of these materials according to the invention and with rapid disintegration properties of the resultant disintegrant-containing tablets.

The invention claimed is:

1. A tablet comprising:
a composition comprising
a co-mixture consisting of 90-98 percent by weight of a sprayed mannitol and 2 to 10 percent by weight of a crosslinked sodium carboxymethylcellulose,
wherein the co-mixture, before being pressed into a tablet, has a BET surface area of greater than 1.5 m$^2$/g,
and wherein the tablet had a hardnesses >250N, a friability ≤0.14% and a disintegration time ≤70 seconds.

2. The tablet of claim 1,
wherein the co-mixture consists of 95 parts by weight of a sprayed mannitol and 5 parts by weight of a crosslinked sodium carboxymethylcellulose.

3. The tablet of claim 1, wherein said co-mixture had a BET surface area from 1.9 to 4.0 m$^2$/g.

4. The tablet of claim 1, wherein said co-mixture had a BET surface area from 1.9 to 2.6 m$^2$/g.

5. The tablet of claim 1, wherein said co-mixture had a bulk density of 0.45 to 0.60 g/ml, a tapped density of 0.60 to 0.75 g/ml, and an angle of repose of 30 to 38°.

6. The tablet of claim 1, wherein said co-mixture had an average particle diameter (laser) between 60 and 200 μm.

7. The tablet of claim 1, wherein said co-mixture had an average particle diameter (laser) between 64 and 114 μm.

8. The tablet of claim 1, wherein said co-mixture had a water content <1% by weight.

9. The tablet of claim 1, wherein said tablet has been formed by compression of the co-mixture at a pressing force of 20 kN.

10. In a tableting process, wherein the improvement is that the excipient is a co-mixture according to claim 1.

11. A tablet comprising an active compound and/or aroma and a co-mixture
wherein said co-mixture consists of 90-98 parts by weight of a sprayed mannitol and 10-2 parts by weight of a crosslinked sodium carboxymethylcellulose,
wherein the co-mixture, before being pressed into a tablet, had a BET surface area of greater than 1.5 m$^2$/g,
and wherein the tablet has a hardnesses >250N, a friability ≤0.14% and a disintegration time ≤70 seconds.

12. The tablet of claim 11, wherein the active compound and/or aroma is one or more vitamins, mineral substances, trace elements, or functional food constituents.

13. The tablet of claim 11, wherein the active compound and/or aroma is one or more plant constituents or plant extracts.

14. The tablet of claim 11, wherein the active compound and/or aroma is one or more synthetic or natural dyes, natural or nature-identical aromas or other flavouring substances, sweeteners, aspartame, sachcharin, acesulfame K, neohesperidin DC, sucralose, thaumatin or stevioside, or fruit aromas, peppermint aromas, menthol, fruit acids, citric acid or tartaric acid or flavouring plant extracts.

15. The tablet of claim 11, wherein the active compound and/or aroma is one or more substances having a pharmacological action, antacids, antiinfectives, analgesics, opioids, antiallergics, antiemetics, or antidiarrheal agents.

16. The tablet of claim 11, which is an orally dispersible tablet.

17. The tablet of claim 11, wherein said tablet has been formed by compression of the active compound and/or aroma and a co-mixture at a pressing force of 20 kN.

18. A method for producing a tablet of claim 11 comprising bringing together the active compound and/or aroma and the co-mixture to form said active compound and/or aroma-containing tablet formulation and compressing the formulation to form a tablet.

19. In a tableting process, wherein the improvement is that an excipient is a co-mixture according to claim 11.

* * * * *